(12) United States Patent
Edelson et al.

(10) Patent No.: US 8,313,945 B2
(45) Date of Patent: *Nov. 20, 2012

(54) METHODS FOR INDUCING THE DIFFERENTIATION OF BLOOD MONOCYTES INTO FUNCTIONAL DENDRITIC CELLS

(75) Inventors: Richard L. Edelson, Westport, CT (US); Carole L. Berger, Bronx, NY (US)

(73) Assignee: Yale University, New Haven, CT (US)

( * ) Notice: Subject to any disclaimer, the term of this patent is extended or adjusted under 35 U.S.C. 154(b) by 409 days.

This patent is subject to a terminal disclaimer.

(21) Appl. No.: 11/804,240

(22) Filed: May 16, 2007

(65) Prior Publication Data

US 2007/0281354 A1 Dec. 6, 2007

Related U.S. Application Data

(63) Continuation-in-part of application No. 10/884,356, filed on Jul. 1, 2004, now abandoned, which is a continuation-in-part of application No. 10/388,716, filed on Mar. 13, 2003, now Pat. No. 7,109,031, which is a continuation-in-part of application No. 10/066,021, filed on Jan. 31, 2002, now abandoned, which is a continuation-in-part of application No. 09/294,494, filed on Apr. 20, 1999, now abandoned.

(51) Int. Cl.
  *C12N 5/07* (2010.01)
  *C12N 5/0784* (2010.01)
(52) U.S. Cl. .................. 435/377; 435/372; 435/325
(58) Field of Classification Search ............... 435/377, 435/372, 325
See application file for complete search history.

(56) References Cited

U.S. PATENT DOCUMENTS 6,008,040 A * 12/1999 Datar ........................... 435/325
2002/0114793 A1   8/2002 Edelson et al.

FOREIGN PATENT DOCUMENTS

| WO | WO 91/13632 | 9/1991 |
| WO | WO 93/20185 | 10/1993 |
| WO | WO 94/11016 | 5/1994 |
| WO | WO 97/34472 | 9/1997 |
| WO | WO 99/38380 | 8/1999 |
| WO | WO 00/62818 | 10/2000 |
| WO | WO 0062818 A1 * | 10/2000 |

OTHER PUBLICATIONS

Jacob et al. 2002. Monocyte-macrophage differentiation in vitro: Modulation by extracellular matrix protein substratum. Molecular and Cellular Biochemistry 233: 9-17.*
Hosein et al. 1985. Monocyte Receptors for Fibronectin Characterized by a Monoclonal Antibody That Interferes With Receptor Activity. J. Exp. Med. vol. 162: 157-170.*
White et al. 2001. Monocyte-Fibronectin Interactions, Via a5b1 Integrin, Induce Expression of CXC Chemokine-Dependent Angiogenic Activity. The Journal of Immunology, 167: 5362-5366.*
Birdsall et al. 2005. Monocytes Stimulated by 110-kDa Fibronectin Fragments Suppress Proliferation of Anti-CD3-Activated T Cells. The Journal of Immunology, 175: 3347-3353.*
Yatohgo et al. Novel Purification of Vitronectin from Human Plasma by Heparin Affinity Chromatography. Cell Structure and Function 13, 281-292 (1988).*
Akagawa et al., Generation of CDI=ReIB=Dendritic Cells and Tartrate-Resistant Acid Phosphatase-Psitive Osteoclast-Like Multinucleated Giant From Human Monocytes, 1996; Blood vol. 88No. 10:4029-4039.
Edelson, Light-Activated Drugs, Scientific American, Aug. 1988, pp. 68-75.
UVAR™ Photopheresis System, 1999. p. 1-11.
PCT Notification of Transmittal of the International Search Report, dated Aug. 9, 2000, PCT/US00/08793.
Notes to form PCT/ISA/220, p. 1-2.
Isolation and Function of Human Dendritic Cells by Lisa Williams, et al.; Copyright 1999.
Review of Human Dendritic Cells: Isolation and Culture from Precursors, pp. 821-837 by Ron Jaffe; Copyright 1993.
Dendritic Cells: Origin and Differentiation by Ranjeny Thomas, et al., Accepted for publication Oct. 30, 1995.
Article published in The Journal of Immunology, entitled—TGF-B1 Promotes In Vitro Generation of Dendritic Cells, etc. By Elisabeth Riedl, et al. vol. 158/Np4/Feb. 15, 1997.
Article published in the Journal of Immunology, entitled TGF-B1 Promotes In Vitro Development of Dendritic Cells, etc. By Herbert Strobl, et al. dated Aug. 15, 1996.
Contrasting Effects of IL-4 and CD40 Ligan on the In Vitro Differentiation of Human Dendritic Cells, etc by B. Canque, et al., date Nov. 15, 1997, published in Blood Magazine by A. Garbe, et al., dated Nov. 15, 1998, vol. 92, No. 10 Supplement (Part 1 of 2).
Abstract #668 from an article entitled: Transforming Growth Factor, etc. published in Blood Magazine by A. Garbe, et al., dated Nov. 15, 1997, vol. 92, No. 10 Supplement 1 (Part of 2).
flt3 Ligand in Cooperation with Transforming Growth Factor, etc. By Herbert Strobl, et al. published in Blood Magazine, vol. 90, No. 4, dated Aug. 15, 1997. pp. 1425-1434.
Berger et al., Induction of human tumor-loaded dendritic cells, 2001, Int. J. Cancer, vol. 91, pp. 438-447.
Berger, C. et al.: "Photopheresis induces monocyte differentiation into functional dendritic antigen presenting cells", Journal of Investigative Dermatology, vol. 112, No. 4, Apr. 1999, p. 580, XP009028191.

(Continued)

*Primary Examiner* — Taeyoon Kim
(74) *Attorney, Agent, or Firm* — McCarter & English LLP

(57) ABSTRACT

Methods are provided for inducing differentiation of blood monocytes into functional antigen presenting dendritic cells. The blood monocytes are treated by exposing the monocytes to proteins adhered to the surface of a treatment device to induce differentiation of the monocytes in to dendritic cells. Differentiation of the monocytes may also be induced by physical perturbation of the monocytes during treatment. The treated monocytes may be co-incubated with disease effector agents, which may be phagocytized by the immature dendritic cells.

6 Claims, 9 Drawing Sheets

OTHER PUBLICATIONS

Glass, et al.: "Cutaneous T-cell Lymphoma", p. 1-13.
International Search Report, Mar. 28, 2005, PCT/US04/07774.
International Search Report, Aug. 22, 2008, PCT/US08/63911.
Berger Carole L et al: "The growth of cutaneous T-cell lymphoma is stimulated by immature dendritic cells." Blood Apr. 15, 2002, vol. 99, No. 8, Apr. 15, 2002, pp. 2929-2939, XP002555202 ISSN: 0006-4971 * p. 2934, right-hand column, paragraph 2—p. 2936, left-hand column *.
Salskov-Iversen Maria et al: "Rapid construction of a dendritic cell vaccine through physical pertubation and apopptotic malignant T cell loading." Journal of Immune Based Therapies and Vaccines Jul. 19, 2005, vol. 3, Jul. 19, 2005, p. 4, XP021008598 ISSN: 1476-8518 * the whole document *.
Supplementary European Search Report dated Nov. 27, 2009 for European Patent Application EP 05 80 2479.
Legitimo, A. et al., "In vitro treatment of monocytes with 8-methoxypsolaren and ultraviolet A light induces dendritic cells with a tolerogenic phenotype.", Clinical and Experimental Immunology, 2007, vol. 148, pp. 564-572; See the summary; p. 565, 1st column, lines 36-55; p. 569, 2nd column, line 3—p. 571, 1st column, line 12.
Girardi, M. et al., "Transimmunization and the evolution of extracorporeal photochemotherapy". Transfusion and Aphresis Science, 2002, vol. 26, pp. 181-190. See abstract.
Berger, C.L. et al., "Transimmunization, a novel approach for tumor immunotherapy". Transfusion and Aphresis Science, 2002, vol. 26, pp. 205-216.
International Search Report in International application No. PCT/US2009/035210 mailed Sep. 11, 2009.

* cited by examiner

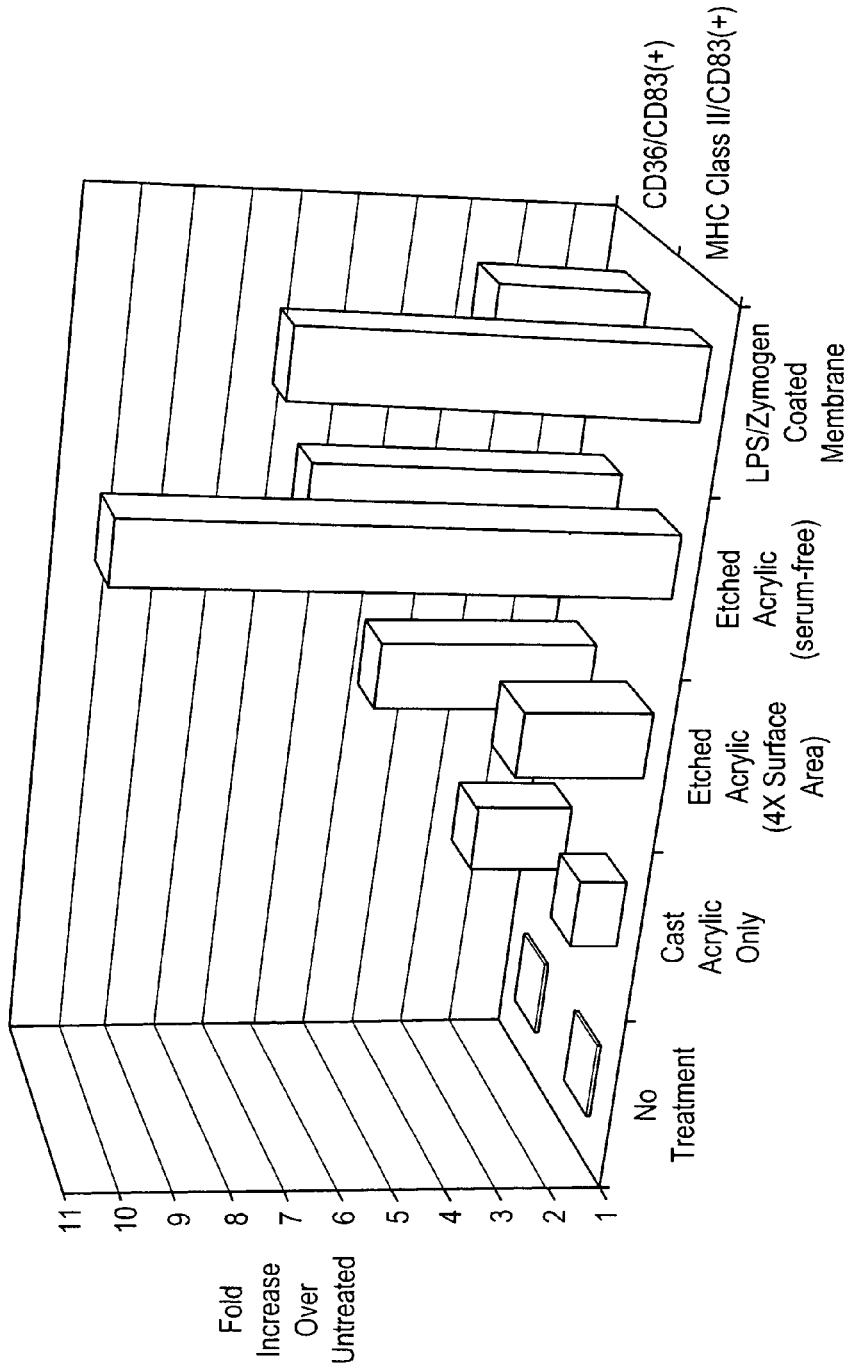

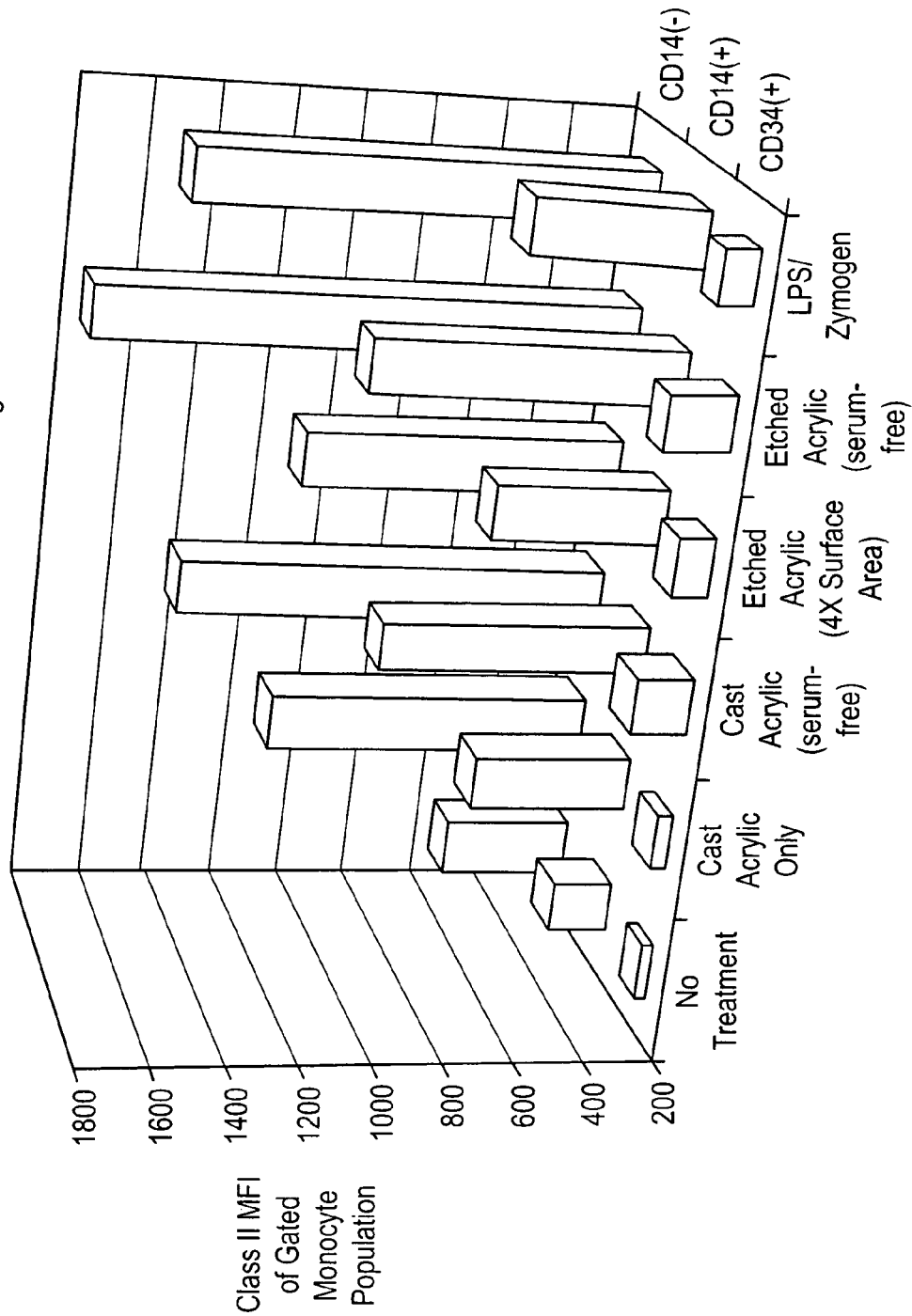

Column effluent contains immature DC containing apoptotic tumor

METHODS FOR INDUCING THE DIFFERENTIATION OF BLOOD MONOCYTES INTO FUNCTIONAL DENDRITIC CELLS

The present application is a continuation-in-part of patent application Ser. No. 10/884,356 filed on Jul. 1, 2004 now abandoned, which is a continuation-in-part of patent application Ser. No. 10/388,716 filed on Mar. 13, 2003 now U.S. Pat. No. 7,109,031, which is a continuation-in-part of patent application Ser. No. 10/066,021 filed on Jan. 31, 2002 now abandoned, which is a continuation-in-part of patent application Ser. No. 09/294,494 filed on Apr. 20, 1999, now abandoned, the entire contents of each of which are hereby incorporated by reference.

FIELD OF THE INVENTION

The present invention relates to methods for producing functional antigen presenting dendritic cells. The dendritic cells are produced by treating an extracorporeal quantity of a subject's blood using a process referred to herein as transimmunization to induce blood monocytes to differentiate into dendritic cells. The functional antigen presenting dendritic cells may be administered to a subject to induce cellular immunologic responses to disease causing agents.

BACKGROUND

Dendritic cells (DCs) are recognized to be powerful antigen presenting cells for inducing cellular immunologic responses in humans, and play a key role in eliciting effective anti-tumor immune responses. DCs prime both CD8+ cytotoxic T-cell (CTL) and CD4+ T-helper (Th1) responses. DCs are capable of capturing and processing antigens, and migrating to the regional lymph nodes to present the captured antigens and induce T-cell responses. In humans, DCs are a relatively rare component of peripheral blood (<1%), but large quantities of DCs can be differentiated from CD34+ precursors or blood monocytes utilizing expensive cytokine cocktails. Alternatively, by treating an extracorporeal quantity of blood using a process referred to herein as transimmunization, a large number of immature DCs can be induced to form from blood monocytes without the need for cytokine stimulation. These immature DCs can internalize and process materials from disease effectors, such as antigens, DNA or other cellular materials, to induce cellular immunologic responses to disease effectors.

Accordingly, the present invention includes methods of producing vaccines comprising dendritic cells loaded with cellular materials to induce cellular immunologic responses to disease effectors.

SUMMARY OF THE INVENTION

A large number of immature dendritic cells are created by treating a quantity of a patient's blood containing monocytes by flowing the blood through narrow plastic channels in a process referred to herein as transimmunization. The physical perturbation caused by the interaction between blood monocytes and the plastic channels induces the monocytes to differentiate and form immature dendritic cells. The monocytes may also be induced to form dendritic cells through interaction with one or more serum protein, such as for example fibronectin or vitronectin, on the walls of the plastic channel.

The present invention also relates to methods for the ex vivo preparation of dendritic cells from blood monocytes. Following physical perturbation of the blood monocytes in the plastic channels or exposure of the monocytes to a serum protein, such as fibronectin or vitronectin on the walls of the plastic channel, the treated blood monocytes may be incubated, exposed to disease effector agents, or both. In several embodiments of the invention, the blood monocytes are subjected to physical perturbation with or without exposure to serum proteins such as fibronectin or vitronectin on the walls of the plastic channels and incubated for a suitable time to allow differentiation to immature dendritic cells. In other aspects the invention relates to preparing dendritic cells from blood monocytes that are exposed to disease effector cells, such as, for example, apoptotic tumor cells, contemporaneously with or after the step of providing physical perturbation. In addition, several aspects of the invention relate to the preparation of dendritic cells through the use of a filtration-type column containing a matrix material, and passing the blood monocytes through the matrix. Although the invention is not limited to any particular mechanism, it is believed that passing the blood monocytes through the narrow column channels created by the matrix material causes physical perturbations, which induce the blood monocytes to differentiate into a dendritic cell phenotype. The effect can be induced or enhanced by including one or more serum proteins, such as a fibronectin or vitronectin, on the walls of the channels. Serum proteins such as fibronectins or vitronectins can provide signals to monocytes, after binding monocyte membrane receptors, helping to stimulate monocyte differentiation into dendritic cells. In some of these aspects, the invention also relates to the exposure of the monocytes to disease effectors, such as, for example, apoptotic tumor cells, either contemporaneously or after passage through the column matrix.

In still another aspect, the invention relates to a method for improving the immunological state of a subject by administering the dendritic cells prepared by the method of the invention back to the same subject.

In yet another aspect, the invention relates to a method for the preparation of T cell regulatory cells (T regs) from normal CD4+ T cells. This method includes the preparation of dendritic cells from a subject's monocytes, and the exposure of the dendritic cells to apoptotic disease effector cells, such as, for example a relatively large ratio of apoptotic tumor cells per dendritic cell, and then incubating these dendritic cells with normal CD4+ T cells. In still another aspect, this invention relates to the administration of Tregs prepared according to this method back to the donor subject for the purpose of improving an immunological state.

BRIEF DESCRIPTION OF THE DRAWINGS

FIG. 10 is a bar chart showing the increase in immature dendritic cells as indicated by the cell markers CD36/CD83 and MHC Class II/CD83 in samples of blood treated in a cast acrylic device, in an etched acrylic device (4× surface area), in an etched acrylic device (4× surface area) serum free, and using a LPS/Zymogen coated membrane.

FIG. 11 is a bar chart showing the increase in the cell surface MHC Class II cell markers in samples of blood treated in a cast acrylic device, in an etched acrylic device (4× surface area), in an etched acrylic device (4× surface area) serum free, and using a LPS/Zymogen coated membrane.

DETAILED DESCRIPTION OF PREFERRED EMBODIMENTS

Figure 1:
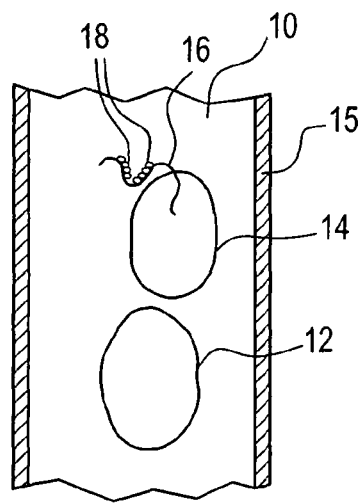
FIG. 1 is a cross-sectional view of a plastic channel containing a blood monocyte from the subject's blood illustrating a CTCL cell with a class I associated antigen, and a blood monocyte.

Dendritic cells are highly effective in presenting antigens to responding T-cells; however, dendritic cells normally constitute less than one percent of blood mononuclear leukocytes. Accordingly, a number of in vitro methods have been developed to expand populations of dendritic cells to augment anti-cancer immunity. By exposing increased numbers of dendritic cells to cellular material, such as for example antigens from tumor or other disease-causing cells, followed by reintroduction of the loaded dendritic cells to the patient, presentation of the cellular material to responding T-cells can be enhanced significantly.

For example, culturing blood mononuclear leukocytes for six to eight days in the presence of granulocyte-monocyte colony stimulating factor (GM-CSF) and interleukin-4 (IL-4) produces large numbers of dendritic cells. These cells can then be externally loaded with tumor-derived peptide antigens for presentation to T-cells. Alternatively, the dendritic cells can be transduced to produce and present these antigens themselves. Expanding populations of dendritic cells transduced to produce and secrete cytokines which recruit and activate other mononuclear leukocytes, including T-cells, has shown some clinical efficacy in generating anti-tumor immune responses.

However, transducing cultivated dendritic cells to produce a particular generic antigen and/or additional cytokines is labor intensive and expensive. More importantly, when used to treat a disease such as cancer, this procedure likely fails to produce and present those multiple tumor antigens that may be most relevant to the individual's own cancer. Several approaches have been proposed to overcome this problem. Hybridization of cultivated autologous dendritic cells with tumor cells would produce tetraploid cells capable of processing and presenting multiple unknown tumor antigens. In a second proposed approach, acid elution of Class I and Class II major histocompatability complexes (MHC) from the surface of malignant cells would liberate a broad spectrum of tumor-derived peptides. These liberated peptides could then be externally loaded onto MHC complexes of autologous cultivated dendritic cells.

Because there are limitations to each of these approaches, an improved method of producing functional antigen presenting dendritic cells and for loading the dendritic cells with cellular material from disease causing agents is desirable. The methods described below improve the efficiency, safety and cost-effectiveness of the production of dendritic cells and the loading of the dendritic cells with antigens and cellular materials for presentation to a subject's immune systems The present invention is based on the convergence of two disparate phenomena: treating blood monocytes in a manner which induces their differentiation into functional dendritic cells, and exposing the dendritic cells to disease effector agents, such as, for example, tumor cells, apoptotic tumor cells or both from a subject. Thus, one aspect of the invention is a method of clinically enhancing a subject's immunity to disease agents that is achieved by combining the treated blood monocytes with the disease effector agents, for example apoptotic tumor cells, for a period of time sufficient to optimize processing and presentation by the dendritic cells of disease associated cellular materials distinctive to the disease effector agents, prior to returning the dendritic cells to the patient.

As used herein, the term "disease effector agents" refers to agents that are central to the causation of a disease state in a subject. In certain circumstances, these disease effector agents are disease-causing cells which may be circulating in the bloodstream, thereby making them readily accessible to extracorporeal manipulations and treatments. Examples of such disease-causing cells include malignant T-cells, malignant B cells, T-cells and B cells which mediate an autoimmune response, and virally or bacterially infected white blood cells which express on their surface viral or bacterial peptides or proteins. Exemplary disease categories giving rise to disease-causing cells include leukemia, lymphoma, autoimmune disease, graft versus host disease, and tissue rejection. Disease associated antigens which mediate these disease states and which are derived from disease-causing cells include peptides that bind to a MHC Class I site, a MHC Class II site, or to a heat shock protein which is involved in transporting peptides to and from MHC sites (i.e., a chaperone). Disease associated antigens also include viral or bacterial peptides which are expressed on the surface of infected white blood cells, usually in association with an MHC Class I or Class II molecule.

Other disease-causing cells include those isolated from surgically excised specimens from solid tumors, such as lung, colon, brain, kidney or skin cancers. These cells can be manipulated extracorporeally in analogous fashion to blood leukocytes, after they are brought into suspension or propagated in tissue culture. Alternatively, in some instances, it has been shown that the circulating blood of patients with solid tumors can contain malignant cells that have broken off from the tumors and entered the circulation. [Kraeft, et al., Detection and analysis of cancer cells in blood and bone marrow using a rare event imaging system, *Clinical Cancer Research*, 6:434-42, 2000.] These circulating tumor cells can provide an easily accessible source of cancer cells which may be isolated, rendered apopototic and engulfed by the dendritic cells in accordance with the method described and claimed herein.

In addition to disease-causing cells, disease effector agents falling within the scope of the invention further include microbes such as bacteria, fungi and viruses which express disease-associated antigens. It should be understood that viruses can be engineered to be "incomplete", i.e., produce distinguishing disease-causing antigens without being able to function as an actual infectious agent, and that such "incomplete" viruses fall within the meaning of the term "disease effector agents" as used herein.

In one embodiment of the methods described herein, the disease effector agents are presented to the dendritic cells after being rendered apoptotic. Any method of isolating disease cells and rendering the cells apoptotic that is known to those skilled in the art may be used. For example, disease effector agents such as cancer cells may be isolated by surgical excision of cells from a patient. Blood borne disease effector cells may be isolated from an extracorporeal quantity of a subject's blood and the isolated cells may be treated to induce apoptosis.

Apoptosis may be induced by adding photo-activated drugs to the disease cells and exposing the cells to light. Cell death can also be induced by exposure of cells to ionizing radiation, for example by exposure to gamma radiation or x-rays utilizing devices routinely available in a hospital setting. Cancer cells may be rendered apoptotic by addition of synthetic peptides with the arginine-glycine-aspartate (RGD) motif cell suspensions of the disease-causing cells isolated from the patient's blood, from excised solid tumors or tissue cultures of the same. RGD has been shown (*Nature*, Volume 397, pages 534-539, 1999) to induce apoptosis in tumor cells, possibly by triggering pro-capase-3 autoprocessing and activation. Similarly, apoptosis could be induced in cells having Fas receptors, by stimulating with antibodies directed against this receptor, in this way sending signals to the inside of the cell to initiate programmed cell death, in the same way that normally Fas ligand does. In addition, apoptosis can be induced by subjecting disease-causing cells to heat or cold shock, certain viral infections (i.e., influenza virus), or bacterial toxins. Alternatively, certain infectious agents such as influenza virus can cause apoptosis and could be used to accomplish this purpose in cell suspensions of disease-causing cells.

The apoptotic cells are exposed to immature dendritic cells, which internalize and process the cellular material. In one embodiment of the invention, the apoptotic cells are produced during the photopheresis procedure through the use of the drug 8-methoxypsoralen and ultraviolet A light and are collected in an incubation bag with the immature dendritic cells, and the apoptotic cells are phagocytosed by the dendritic cells during the incubation period. The resulting dendritic cells are then administered to the patient to induce an immune response to the disease causing agent.

Induction of Monocyte Differentiation into Dendritic Cells

As noted above, in one embodiment, monocyte differentiation is initiated by exposing the monocytes contained in an extracorporeal quantity of a subject's blood to the physical forces resulting from the sequential adhesion and release of the monocytes on plastic surfaces, such as the surfaces of the channels of a conventional photopheresis device. In another embodiment, the plastic surfaces include a protein, such as a fibronectin, adhered to the surface of the plastic surface. Proteins such as fibronectins can bind monocyte membrane receptors and provide signals to monocytes to induce differentiation of the monocytes into dendritic cells.

It should be noted that these processes, physical perturbation and interaction with serum proteins, may be performed simultaneously and work in a complementary manner to induce differentiation of blood monocytes into dendritic cells.

In one embodiment of the invention, a white blood cell concentrate is first prepared in accordance with standard leukapheresis practice using a leukapheresis/photopheresis apparatus of the type well known to those skilled in the art. The white blood cell concentrate includes monocytes, lymphocytes and some red blood cells and platelets. Typically, up to two billion white blood cells are collected during leukapheresis. Assuming that monocytes comprise from about 2% to about 50% of the total white blood cell population collected, approximately 40 million to 1 billion monocytes are present in the white blood cell concentrate. It should be understood that the methods are not limited to use of blood first treated by leukapheresis, and whole blood may be used in the methods described herein.

Following separation by leukapheresis, monocyte differentiation is induced by pumping the blood cell concentrate through a device which has a plurality of plastic channels. Preferably, the plastic channels have a diameter of between about 0.5 mm and 5.0 mm. In one embodiment, a conventional photopheresis apparatus having a channel diameter of 1 mm or less is used. The narrow channel configuration of the photopheresis apparatus maximizes the surface area of plastic to which the blood cell concentrate is exposed as it flows through the photopheresis apparatus. The invention is not limited in this regard, however, and any appropriate device having plastic channels may be used to induce monocyte differentiation.

Treatment of Monocytes Using Conventional Photopheresis Apparatus

In one embodiment of the present invention wherein the white blood cell concentrate is treated using a photopheresis apparatus, monocyte differentiation is induced by the physical forces experienced by the monocytes as they flow through the plastic channels in the photopheresis apparatus. While the invention is not limited to any particular mechanism, the inventors believe that monocytes in the blood cell concentrate are attracted to the plastic channel walls of the photopheresis apparatus, and the monocytes adhere to the channel walls. The fluid flow through the channel imposes shearing forces on the adhered monocytes that cause the monocytes to be released from the plastic channel walls. Accordingly, as the monocytes pass through the photopheresis apparatus, they may undergo several episodes of adherence to and release from the plastic channel walls. These physical forces send activation signals though the monocyte cell membrane, which results in induction of differentiation of monocytes into immature dendritic cells that are aggressively phagocytic.

In another embodiment of the invention, the plastic surfaces include one or more adhered serum proteins, such as a fibronectin or vitronectin. As the monocytes flow through the treatment device, the monocytes interact with the fibronectin or vitronectin on the plastic surface. The fibronectin or vitronectin adhered on the surface of the plastic transmits signals to the monocytes flowing past causing the monocytes to differentiate into dendritic cells.

Inducing monocytes to form dendritic cells by these methods offers several advantages for immunotherapeutic treatment. Because all of the dendritic cells are formed from the monocytes within a very short period of time, the dendritic cells are all of approximately the same age. Dendritic cells will phagocytize apoptotic cells during a distinct period early in their life cycle. In addition, the antigens present in the phagocytized apoptotic cells are processed and presented at the surface of the dendritic cells during a later distinct period. By creating dendritic cells with a relatively narrow age profile, the method of the present invention provides an enhanced number of dendritic cells capable of phagocitizing apoptotic disease effector agents and subsequently presenting antigens from those disease effector agents for use in immunotherapeutic treatment.

Following treatment to initiate differentiation of monocytes, the treated blood cell concentrate may be sequestered for incubation in the presence of apoptotic cells delivered to the dendritic cells. The incubation period allows the dendritic cells forming and maturing in the blood concentrate to be in relatively close proximity to the apoptotic cells, thereby increasing the likelihood that the apoptotic cells will be engulfed and processed by the dendritic cells. A standard blood bag may be utilized for incubation of the cells, as is typical in photopheresis. However, it has been found to be particularly advantageous to use a blood bag of the type which does not leach substantial amounts of plasticizer and which is sufficiently porous to permit exchange of gases, particularly $CO_2$ and $O_2$. Such bags are available from, for example, the Fenwall division of Baxter Healthcare Corp. under the name Amicus™ Apheresis Kit. Various plasticizer-free blood bags are also disclosed in U.S. Pat. Nos. 5,686,768 and 5,167,657, the disclosures of which are herein incorporated by reference.

The treated blood cell concentrate and disease effector agents are incubated for a period of time sufficient to maximize the number of functional antigen presenting dendritic cells in the incubated cell population. Typically, the treated blood cell concentrate and disease effector agents are incubated for a period of from about 1 to about 24 hours, with the preferred incubation time extending over a period of from about 12 to about 24 hours. Additional incubation time may be necessary to fully mature the loaded DC prior to reintroduction to the subject. Preferably, the blood cell concentrate and disease effector agents are incubated at a temperature of between 35 degrees Centigrade and 40 degrees Centigrade. In a particularly preferred embodiment, the incubation is performed at about 37 degrees Centigrade. By treating monocytes in the manner described above and then incubating the treated cell population with the disease effector agents, a large number of functional antigen presenting dendritic cells can be obtained. The activated monocytes produce natural cytokines which aid in the differentiation of the monocytes into dendritic cells. Alternatively, a buffered culture medium may be added to the blood bag and one or more cytokines, such as GM-CSF and IL-4, during the incubation period. Maturation cocktails (typically consisting of combinations of ligands such as CD4OL; cytokines such as interferon gamma, TNF alpha, interleukin 1 or prostaglandin E2; or stimulatory bacterial products) may be added to ensure production of fully functional mature DC.

The application of one embodiment of the method described above is illustrated in FIGS. 1 to 7. FIGS. 1 to 7 illustrate treatment of individual cells, but it should be understood that in practice a plurality of blood monocytes will be converted to dendritic cells, and that the plurality of dendritic cells will interact with a plurality of T-cells. Referring to FIG. 1, a plastic channel 10 contains a quantity of the subject's blood, or the blood cell concentrate if the subject's blood is first treated by leukapheresis. The blood contains blood monocytes 12 and is pumped through the plastic channel to induce differentiation of the monocytes into dendritic cells. The blood may also contain disease effector agents, such as, for example, a CTCL cell 14 with a class I associated antigen 16.

Figure 2:
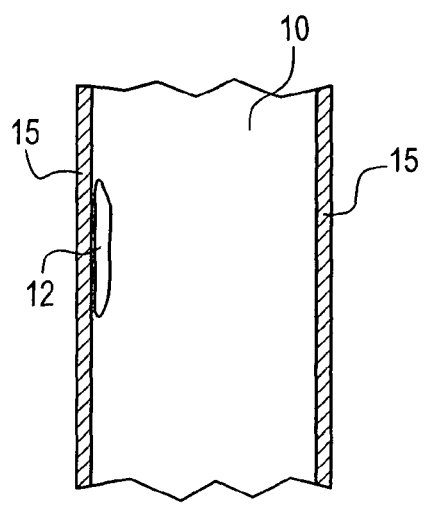
FIG. 2 is a cross-sectional view of a plastic channel containing the subject's blood illustrating a blood monocyte adhered to the wall of the plastic channel.
Figure 3:
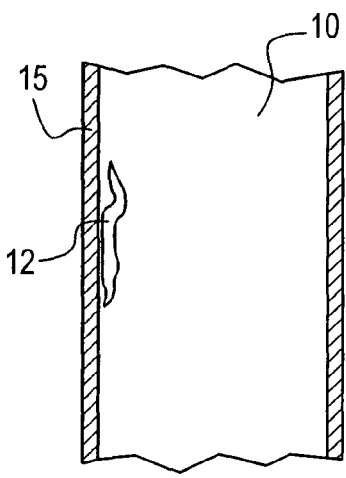
FIG. 3 is a cross-sectional view of a plastic channel containing the subject's blood illustrating a blood monocyte partially adhered to the wall of the channel.
Figure 4:
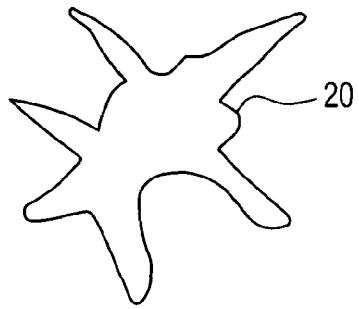
FIG. 4 is an illustration of dendritic cell produced by differentiation of a blood monocyte by the method of the present invention.

As shown in FIG. 2, as the subject's blood is pumped though the plastic channel, monocytes 12 adhere to the inner walls 15 of the plastic channel 10. Shear forces are imposed on the adhered monocytes by the fluid flowing past the monocytes and, as shown in FIG. 3, the monocytes 12 become dislodged from the wall 15. As the monocytes flow through the plastic channel, they may undergo several episodes of adherence and removal from the channel walls. As a result of the forces experienced by the monocyte, activation signals are transmitted which cause the monocyte to differentiate and form an immature dendritic cell 20, illustrated in FIG. 4. As discussed above, in one embodiment, the plastic channel is part of a conventional photopheresis apparatus.

After the blood has been passed through the plastic channel, the subject's blood is incubated in the presence of disease effector agents, such as for example apoptotic cancer cells, to allow phagocytosis of the apoptotic cells and subsequent maturation of the dendritic cells. As the dendritic cell continues to mature during the incubation period, it processes the apoptotic cells. Although not limiting to the present invention, the inventors believe that by the end of the incubation period, the dendritic cell has digested the apoptotic cells, processed the proteins obtained from the apoptotic cellular materials, and is presenting those antigens at the surface of the dendritic cell. After the incubation period, the composition containing the antigen presenting dendritic cells is reinfused into the subject for immunotherapy.

Figure 5:
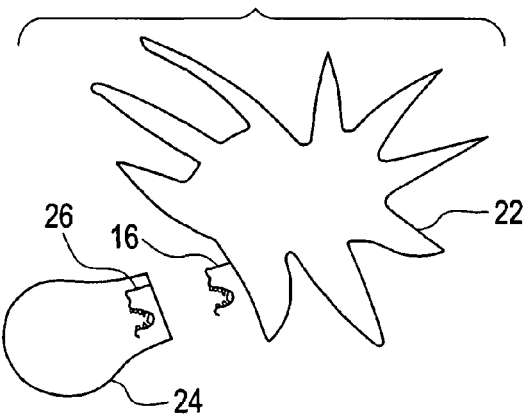
FIG. 5 is an illustration of a dendritic cell which has been reinfused into the subject's bloodstream presenting a class 1 associated peptide antigen to a T-cell.
Figure 6:
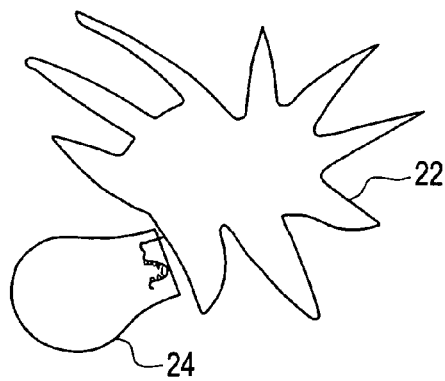
FIG. 6 is an illustration of the class 1 associated peptide antigen presented on the surface of the dendritic cell as it is received by a complementary receptor site on the T-cell.
Figure 7:
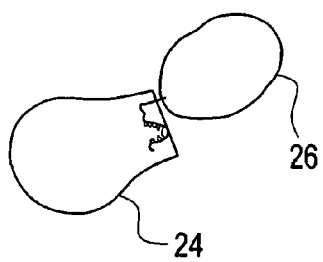
FIG. 7 is an illustration of a clone of the activated T-cell attacking a disease-causing cell displaying the class 1 associated peptide antigen.

Referring now to FIGS. 5 and 6, which illustrate the dendritic cell after reinfusion into the subject's blood stream, the dendritic cell 22 presents at its surface antigens 16 from the cellular material to a healthy T-cell 24 which has a receptor site 26 for the antigen 16. When the healthy T-cell 24 receives the antigen from the dendritic cell, as shown in FIG. 6, the healthy T-cell is activated and induces the formation of T-cell clones which will recognize and attack disease effectors displaying the antigen. As a result, as shown in FIG. 7, the healthy T-cell clones 24 of the subject's immune system are triggered to recognize the antigen displayed by the disease effector agent, and to attack and kill disease cells 26 in the subject which display the same antigen.

It should be understood that it is not absolutely necessary to separate the monocytes from the extracorporeal quantity of the patient's blood by leukapheresis prior to treatment. As long as the monocytes contained in the blood are sufficiently exposed to physical forces imposed by flow through plastic channels to initiate differentiation into dendritic cells followed by subsequent incubation, separation of the monocyte population is not required.

Inducing monocyte differentiation according to the method described above provides dendritic cells in numbers which equal or exceed the numbers of dendritic cells that are obtained by expensive and laborious culture of leukocytes in the presence of cytokines such as GM-CSF and IL-4 for seven or more days. The large numbers of functional dendritic cells generated by the method described above provide a ready means of presenting selected material, such as, for example, apoptotic cells, disease agents, antigens, plasmids, DNA or a combination thereof, and are thereby conducive to efficient immunotherapy. Antigen preparations selected to elicit a particular immune response may be derived from, for example, tumors, disease-causing non-malignant cells, or microbes such as bacteria, viruses and fungi. The antigen-loaded dendritic cells can be used as immunogens by reinfusing the cells into the subject or by otherwise administering the cells in accordance with methods known to elicit an immune response, such as subcutaneous, intradermal or intramuscular injection. As described below, it is also possible to generate antigen-loaded dendritic cells by treating and co-incubating monocytes and disease effector agents which are capable of expressing disease associated antigens.

Treatment of Monocytes Using Plastic Treatment Apparatus

In another embodiment of the invention, monocyte differentiation is induced by pumping a blood leukocyte preparation containing monocytes through a plastic treatment apparatus. The plastic treatment apparatus used to treat the monocytes to induce monocyte differentiation may be comprised of any plastic material to which the monocytes will transiently adhere and that is biocompatible with blood leukocyte cells. Examples of materials that may be used include acrylics, polycarbonate, polyetherimide, polysulfone, polyphenylsulfone, styrenes, polyurethane, polyethylene, Teflon or any other appropriate medical grade plastic. In a preferred embodiment of the present invention, the treatment device is comprised of an acrylic plastic.

In the monocyte treatment apparatus, the leukocyte preparation flows through narrow channels. Narrow channels are used to increase the probability and frequency of monocyte contact with the interior plastic surface of the treatment apparatus. The narrow channels also result in flow patterns through the treatment apparatus which impose shearing forces to monocytes transiently contacting or adhering to the interior plastic surfaces of the treatment apparatus.

Figures 8, 9:
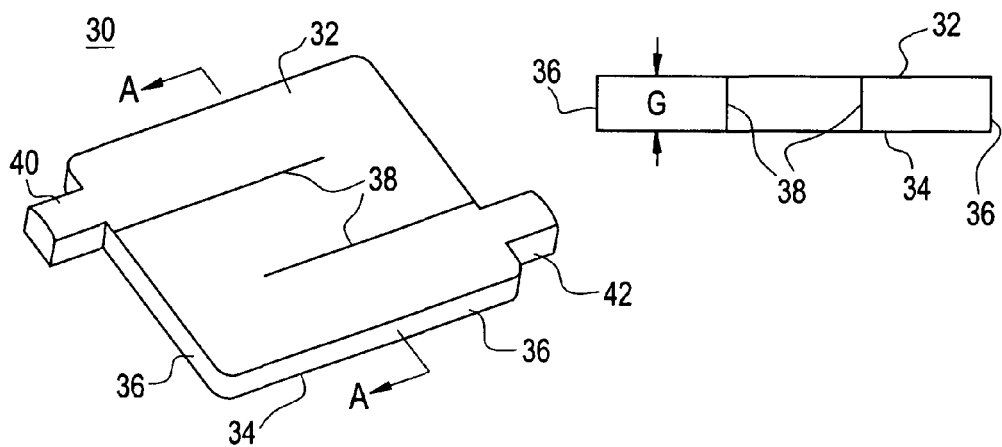
FIG. 8 is a side view of a plastic treatment apparatus which may be used to induce monocyte differentiation into functional antigen presenting dendritic cells.
FIG. 9 is a view of cross section A-A of the plastic treatment apparatus of FIG. 8.

Referring now to FIGS. 8 and 9, one embodiment of a plastic monocyte treatment apparatus is shown. In this embodiment, the treatment apparatus 30 comprises a top plate 32, a bottom plate 34 and side walls 36 to form a box-like structure having a gap, G, between the top plate 32 and the bottom plate 34 to form a narrow channel for flow of blood leukocyte preparations. The top plate 32 and the bottom plate 34 are comprised of a plastic material, such as acrylic or other suitable medical grade plastic as described above.

The side walls 36 of the treatment apparatus may be comprised of the same material as the top plate 32 and the bottom plate 34. Alternatively, the side walls 36 may be comprised of any material, such as for example a rubber, that will form a seal between with the top plate and the bottom plate. The treatment apparatus may have any desired outer shape. For example, the treatment apparatus may have rounded corners, or it may be round or oval.

The top plate 32, bottom plate 34 and side walls 36 may be fastened together using any fastening method known to those skilled in the art. For example, the top plate and bottom plate may be glued to the side walls. Alternatively, bolts, rivets or other fasteners may be used to assemble the top plate, bottom plate and side walls. Gaskets or other sealing materials may be used as necessary to seal the treatment apparatus to prevent leakage.

Internal walls 38 may be provided to direct the flow of the monocytes through the device. The internal walls are typically made of the same material as the top plate and the bottom plate. The internal walls direct the flow of the leukocyte preparation through the treatment apparatus, prevent channeling of flow through the treatment apparatus, and increase the plastic surface area that the monocytes are exposed to within the treatment apparatus. The number of internal walls and the arrangement of the internal walls may be varied to achieve the desired flow pattern through the treatment device. The available surface area may also be increased by including one or more plastic dividers or posts in the flow path through the narrow channels of the plastic treatment apparatus.

The total surface area available for monocyte interaction may also be increased by passing leukocytes through a closed plastic treatment apparatus containing plastic or metal beads. These beads increase the total surface area available for monocyte contact and may be composed of iron, dextran, latex, or plastics such as styrenes or polycarbonates. Beads of this type are utilized commercially in several immunomagnetic cell separation technologies and are typically between 0.001 and 10 micrometers in size, although the invention is not limited in this regard and any appropriate bead may be used. Unmodified beads or those coated with immunoglobulins may also be utilized in this embodiment.

Referring again to FIG. 8, the monocytes enter the treatment apparatus through an inlet connection 40, flow through the treatment apparatus and exit through an outlet connection 42. A pump (not shown) may be used to induce flow through the treatment apparatus, or the treatment apparatus may be positioned to allow gravity flow through the treatment apparatus. The inlet connection 40 and outlet connection 42 may be separate components that are fastened to the treatment apparatus, or they may be made of the same material as the treatment apparatus and formed as an integral part of the top and bottom plates or the side walls.

The top plate 32 and the bottom plate 34 are spaced apart to form a gap G that is preferably between about 0.5 mm and about 5 mm. The total volume of the treatment apparatus is preferably between 10 ml and about 500 ml but may vary depending on the application and blood volume of the mammalian species. Preferably, the leukocyte fraction is pumped through the treatment apparatus at flow rates of between about 10 ml/min and about 200 ml/min. Shearing forces are typically in the range associated with mammalian arterial or venous flow but can range from 0.1 to 50 dynes/cm$^2$. The invention is not limited in this regard, and the volume of the treatment apparatus and the flow rate of the leukocyte preparation through the treatment apparatus may vary provided that sufficient shearing forces are imposed on monocytes contacting the walls of the treatment apparatus to induce monocyte differentiation into functional dendritic cells.

The interior surfaces of the treatment device may be modified to increase the available surface area to which the monocytes are exposed. The increased surface area increases the likelihood that monocytes will adhere to the interior surface of the treatment apparatus. Also, the modified surface may influence the flow patterns in the treatment apparatus and enhance the shearing forces applied to monocytes adhered to the interior surface by the fluid flowing through the treatment apparatus. The interior surfaces of the treatment apparatus may be modified by roughening the surface by mechanical means, such as, for example, by etching or blasting the interior surfaces using silica, plastic or metal beads. Alternatively, grooves or other surface irregularities may be formed on the plastic surfaces during manufacturing. The enclosed exposure area through which the monocytes flow may also consist of a chamber whose contents include beads of various compositions to maximize surface area exposure. The invention is not limited in this regard, and the interior surface or contents of the treatment apparatus may be by any other appropriate method known to those skilled in the art.

In another embodiment of the present invention, plasma and serum proteins are removed from the blood leukocyte preparation prior to passing the leukocytes through the treatment device. Blood proteins, such as hemoglobin, albumins, etc., and cellular components such as platelets or red blood cells, can potentially adhere to the interior plastic surface of the treatment device, thereby creating a surface coating which reduces or prevents monocyte interaction with the plastic surface. By removing serum proteins from the leukocyte preparation prior to pumping the leukocyte preparation through the treatment apparatus, contamination of the plastic surfaces by plasma or serum proteins is reduced or eliminated. Reduction or elimination of this surface contamination increases the available surface area for monocyte interaction.

In this embodiment of the invention, an extracorporeal quantity of blood is treated by leukapheresis to obtain a leukocyte concentrate. The leukocyte concentrate is then further treated to remove plasma and serum proteins from the leukocyte concentrate. The serum may be separated from the leukocytes by performing an additional centrifugal elutriation, density gradient or immunoselection. Centrifugal elutriation may be carried out using a variety of commercially available apheresis devices or one specifically designed for the invention. Density gradients include, but are not limited to, Ficoll Hypaque, percoll, iodoxanol and sodium metrizoate. Immunoselection of purified monocytes may also be utilized to remove contaminating proteins and non-monocyte leukocytes prior to exposure to the device. Alternatively, the leukocyte preparation may be treated by any other method known to those skilled in the art to separate mononuclear cells from other blood components Following removal of serum or plasma components, the leukocyte preparation is pumped through a plastic monocyte treatment apparatus as described above to induce monocyte differentiation into dendritic cells. After the leukocyte preparation is pumped through the treatment apparatus, it is incubated for an appropriate period of time to allow the treated monocytes to differentiate into functional dendritic cells. During this time, immature dendritic cells may be loaded with exogenous antigens including those from whole cells, proteins or peptides. The treated monocytes are typically incubated for a period of between about 12 hours and about 36 hours.

The efficacy of the methods described above are demonstrated by the data shown in FIGS. 10 and 11. This data was obtained using a small plastic treatment apparatus to treat samples of peripheral blood containing monocytes. The treatment apparatus used in these tests had acrylic top plates and bottom plates which were bolted together. The treatment apparatus had a single channel of 30 by 3 cm dimension, 1 mm interplate gap and a total void volume of approximately 10 ml. The leukocyte concentrate was pumped through the treatment apparatus at a flow rate of about 50 ml/minute for 30 minutes. The treated cells incubated overnight to allow differentiation of monocytes into functional dendritic cells.

The data illustrated in FIGS. 10 and 11 was obtained by treating peripheral blood in (1) a treatment apparatus having an unmodified cast acrylic panel; (2) a treatment apparatus having an acrylic panel etched with silica beads to increase the surface area of the panel by a factor of approximately four; and (3) a treatment apparatus having an etched acrylic panel and serum-free peripheral blood monocytes (PBMC) isolated over Ficoll Hyplaque. The conversion of blood monocytes to immature dendritic cells was measured by using previously established markers of dendritic cell development, including cell surface MHC class II and CD36 and intracellular production of CD83.

As shown in FIGS. 10 and 11, treatment of peripheral blood in a cast acrylic treatment apparatus approximately doubled the population of immature dendritic cells in the samples as compared to untreated blood. When the interior surface of the acrylic treatment apparatus was etched to increase the surface area, treatment of the peripheral blood approximately tripled the population of immature dendritic cells as compared to untreated blood. Treatment of peripheral blood with the serum removed prior to treatment increased the population of dendritic cells by a factor of up to eight as compared to untreated blood.

These results demonstrate that treatment of peripheral blood monocytes by pumping the monocytes through a plastic treatment apparatus having narrow channels is an effective method of inducing monocyte differentiation into functional dendritic cells. Etching the surface of the treatment apparatus and removing plasma and serum from the peripheral blood being treated can further enhance the population of dendritic cells obtained.

In another embodiment of the present invention, peripheral blood monocytes are pumped through a treatment apparatus similar to that described above, with at least one interior surface of the treatment apparatus comprising a membrane or surface coated with either pathogen associated inflammatory molecules such as LPS and Zymogen, or with known monocyte ligands that interact with monocyte adhesion molecules (including, for example, E-selectin, ICAM-1, Fractalkine or MCAF/CCC2). As the monocytes in the peripheral blood flow through the treatment apparatus, the monocytes are exposed to these proteins. The stimulatory surface interaction between these molecules and the monocytes induces monocyte differentiation into functional dendritic cells. As shown in FIG. 10, the dendritic cell population in peripheral blood samples treated by exposing the monocytes to an LPS/Zymogen coated membrane is comparable to the increased population observed by treatment of a serum-free blood in an etched acrylic treatment apparatus. It will be recognized that this embodiment of the invention is not limited to use of LPS and Zymogen, the treatment apparatus may include any protein that can be crosslinked to solid supports such as nylon membranes or plastic surfaces and will interact with blood monocytes to induce differentiation into functional dendritic cells. Proteins which can be absorbed to solid supports and used to induce monocyte differentiation include, but are not limited to, inflammatory molecules, adhesion molecules, cytokines, chemokines or serum proteins known to affect leukocyte adhesion and activation.

Among the advantages of this embodiment of the invention are that the treatment time is reduced, as no incubation is required after treatment of the extracorporeal quantity of blood; If desired, the treatment can be combined with radiation or chemotherapeutic treatments in one procedure, thereby reducing the number of times a particular subject must appear for treatment.

After the extracorporeal quantity of the patient's blood has been treated in the plastic treatment device, the composition is incubated for a period of from about 1 to about 48 hours, most preferably from about 12 to about 24 hours. During this period, the dendritic cells phagocytize apoptotic cells and present antigens from the phagocytized cells at their surface, where they will be recognized by T-cells in the patient's immune system, thereby inducing an immunological response to the disease effector agents in the patient.

Induction of Monocyte Differentiation Using a Tube or Packed Column

Other embodiments of the present invention include methods for inducing monocyte differentiation into dendritic cells (DCs) by exposing monocytes contained in an extracorporeal quantity of the recipient's whole or leukaphoresed blood to physical perturbation in a device such as a plastic tube or a packed filtration column containing a matrix of beads or some other appropriate packing material that forms narrow channels through the column. In another embodiment of the present invention the monocytes are treated to induce differentiation and the treated cells are exposed to, or incubated with, disease effector agents.

In one embodiment of the methods of the present invention, monocyte differentiation is induced by obtaining an extracorporeal quantity of whole blood or leukaphoresed blood from a patient, and disposing the blood into a closed plastic container, such as for example a plastic tube. The plastic container may be comprised of any appropriate plastic known to those skilled in the art to which monocytes will adhere, such as, for example, acrylics, polycarbonate, poly etherimide, polysulfone, styrenes, polyethylene or polyurethane. The blood contained in the tube is subjected to physical perturbation, such as for example by centrifugation or agitation by shaking the tube mechanically or manually. The blood contained in the plastic container is subjected to the physical perturbation for a sufficient time, typically from about 15 minutes to about 3 hours at a temperature of about 10 degrees Centigrade to about 50 degrees Centigrade to induce monocytes contained in the blood to differentiate into DCs. Preferably, the blood is subjected to the physical perturbation for about 30 minutes to about 2 hours at a temperature of about 20 degrees Centigrade to about 40 degrees Centigrade. In a preferred embodiment the blood is subjected to the physical perturbation for about 30 minutes to about 1 hours at a temperature of about 20 degrees Centigrade to about 37 degrees Centigrade. In another preferred embodiment, the blood is placed in a plastic container and rotated in a tube rotator for a period of about 1 hour, at about 37 degrees Centigrade, at from about 10 RPM to about 50 RPM. Optionally, the treated blood may be incubated overnight as described previously herein, either with or without disease effector agents, such as apoptotic disease cells, added to the treated blood.

In other embodiments of the method of the present invention, a packed column is used to treat the blood to induce differentiation of monocytes into DCs. The body of the column may be comprised of a polymeric material to which the monocytes may adhere, for example a plastic such as the plastics described above, or the body of the column may be substantially comprised of a non-plastic material and have an interior polymeric lining, coating of plastic, or other material that provides for sufficient binding, and physical perturbations to induce monocyte differentiation. The invention is not limited in this regard, and any column material may be used that does not interfere with the treatment of the monocytes by interaction with the packing materials.

The column is packed with a packing material that will cause physical perturbation of the monocytes as they pass through the column. In a preferred embodiment, the column packing is a material to which the monocytes will undergo sequential adhesion and release as the blood flows through the column packing. For example, matrix materials used for column packing may include sepharose, dextran, latex, cellulose acetate, acrylics, polycarbonate, polyetherimide, polysulfone, styrenes, polyurethane, polyethylene, Teflon or any combination thereof. The packing is preferably in the form of spherical beads, although any shape may be used that will produce flow of the monocytes through channels. When spherical beads are used, the beads should be an appropriate size to produce the desired porosity and flow characteristics to induce monocyte differentiation. In preferred embodiments, the beads have an average diameter of about 1 micron to about 10 microns.

The volume of the column is from about 1.0 ml to about 500 ml, but it may vary depending on the treatment application. The flow rate of the whole blood or leukocyte concentrate through the channels in the column matrix is dependent on a plurality of variables, for example, gravity, the relative viscosity of the fluid in the column, the relative density and/or porosity of the column matrix, the material comprising the column matrix, and other factors that will be apparent to those of ordinary skill in the art. For example, the flow rate may be from about 1 ml per minute for a drip column to about 50 ml per minute for a pumped column. The blood passes through the column apparatus at a sufficient rate to cause physical perturbation to the blood monocytes sufficient to induce differentiation into dendritic cells. For example, the flow through the column may produce shearing forces on monocytes adhered to the column packing, resulting in sequential adhesion and release of blood monocytes from the column packing. The optimum flow rate will result in a physical force sufficient to promote differentiation of the monocytes into dendritic cells without causing hemolysis, and can easily be determined by those skilled in the art.

Preliminary evidence suggests that interaction of monocyte β-glycoprotein with the plastic surface may contribute to the monocyte entry into the dendritic cell maturational pathway. Therefore, it may be possible to induce monocyte-to-dendritic cell maturation by direct interaction with monocyte β-glycoprotein, without use of a plastic flow system.

There are several commercially available columns that may be used in the method of the invention, such as for example the Miltenyi Biotec (Auburn, Calif.) MACS LS™ Separation column, which uses an iron-containing matrix and conjugated magnetic micro-beads, or the Adacolumn® sold by Japan Immunoresearch Laboratories Co., Ltd. The Adacolumn® is an extracorporeal leukocyte apheresis device, specifically a single use direct blood perfusion type apheresis column that is filled with specially designed cellulose acetate beads, and has been used for the selective retention of granulocytes, and monocytes/macrophages. When used for selective retention of granulocytes and monocytes/macrophages, blood can be drawn into the column from a first vein of a patient, and returned to the patient via a second vein, without using a shunt. The column typically retains 40%-50% of the monocyte population in the blood entering the column. The remaining blood monocytes which pass through the column are subjected to physical perturbation and can undergo differentiation into dendritic cells. The treated blood may be incubated to allow the treated monocytes to mature into functional dendritic cells. Incubation may take place in the presence of apoptotic disease cells.

In yet another embodiment of the present invention, disease cells may be isolated from whole blood or leukaphoresed blood using a column having a packing that is labeled to attract the disease cells. The disease cells retained by the labeled packing material may be rendered apoptotic and then added to previously treated blood monocytes, or the monocytes contained in the patient's blood may be induced to differentiate in the packed column at the same time that the disease cells are rendered apoptotic.

For example, in one aspect of this embodiment of the invention, CD4 expressing (CD4+) CTCL cells are isolated from whole blood or from leukaphoresed blood cells, such as for example, through the use of a MACS LS Separation Column™ (Miltenyi Biotec, Auburn, Calif.). The MACS separation column works by retaining magnetic-bead labeled cells within the column matrix using a magnetic field while allowing unlabeled cells to pass through. The cells retained in the column, and any cells bound to them, can be eluted by removing the column from the magnetic field and eluting the beads using any appropriate solution. The eluting solution may be forced through the beads with a plunger. In this aspect of the invention, whole blood or leukapheresed blood cells are incubated with a CD4 antibody-conjugated (CD4ab) material, typically CD4ab-magnetic beads (from about 1 million to about 6 million per ml), in a suitable container; followed by packing the CD4ab-magnetic bead-CTCL cell complex into a magnetic filtration column; washing with a suitable volume of a suitable buffer; for example phosphate buffered saline containing EDTA and bovine serum albumin, and subsequent elution with a plunger. The purified, eluted CTCL cells can then be rendered apoptotic, for example by treatment with gamma radiation, drugs, or antibodies, and cultured ex vivo in a eukaryotic cell incubator in the presence of activated monocytes, which have begun transitioning into DCs. The invention is not limited to isolation of CTCL cells, and it will be understood by those skilled in the art that this method can be used to isolate other disease cells which can be separated by using beads labeled with an appropriate antibody or other molecule used to attract the particular disease cell.

In another aspect of this embodiment of the invention, isolated disease cells may be rendered apoptotic. For example, in one embodiment of the invention, CTCL cells isolated using the method for packed column purification of CD4+ CTCL cells outlined above may be incubated with CD3ab (at about 33 µg/ml) for a period of about 1 minute to about 90 minutes, at from about 10 degrees Centigrade to about 40 degrees Centigrade. Preferably, the CTCL cells are incubated with CD3ab for a period between about 20 minutes to about 40 minutes, and at a temperature between about 15 degrees Centigrade to about 30 degrees Centigrade. The CD3ab substantially induces apoptosis in the CTCL cells. The apoptotic CTCL cells (from about 1 million to about 6 million) may then be incubated with treated monocytes that are in the process of differentiation into dendritic cells.

Figure 12A:
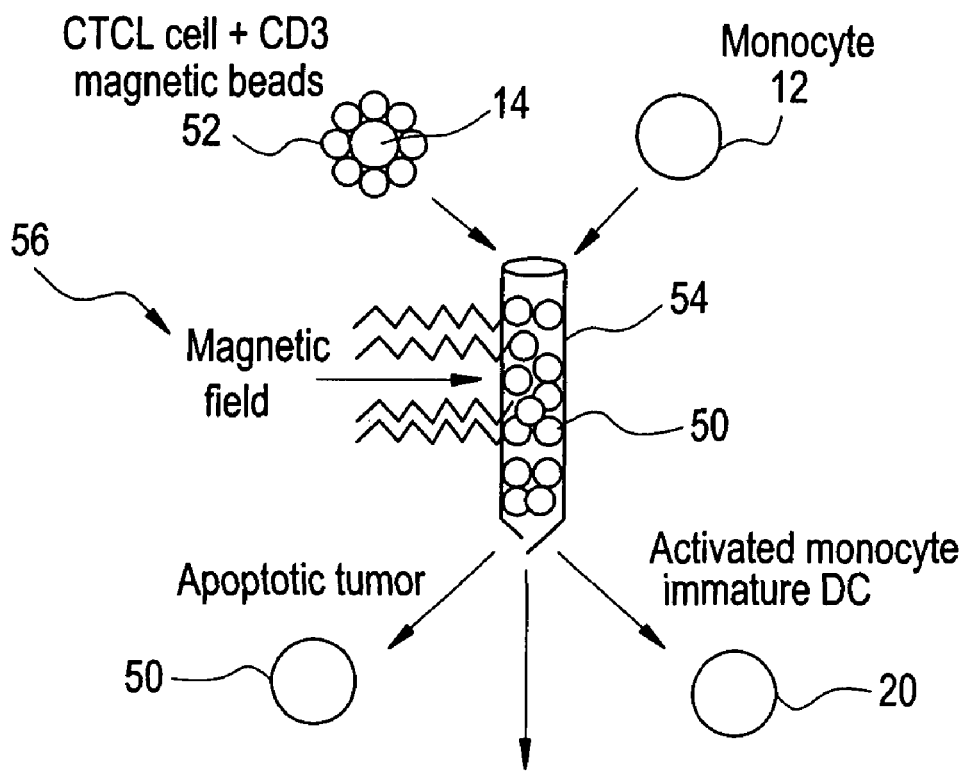
FIG. 12, (a) is an illustration representing one embodiment of the present invention. CTCL cells are coated with CD3antibody-conjugated magnetic beads rendering them apoptotic; the CD3ab-bead-coated CTCL cells are passed through column and bound by a magnetic field; monocytes can be passed through the column substantially contemporaneously with the CD3ab-bead-coated CTCL cells or afterwards. The column effluent will contain DCs ingesting apoptotic tumor cells; (b) is a graph showing the frequency of obtaining semi-mature DCs in the absence of apoptotic tumor cells, and (c) is a graph showing the frequency of obtaining semi-mature DCs in the presence of apoptotic tumor cells.
Figure 12B:
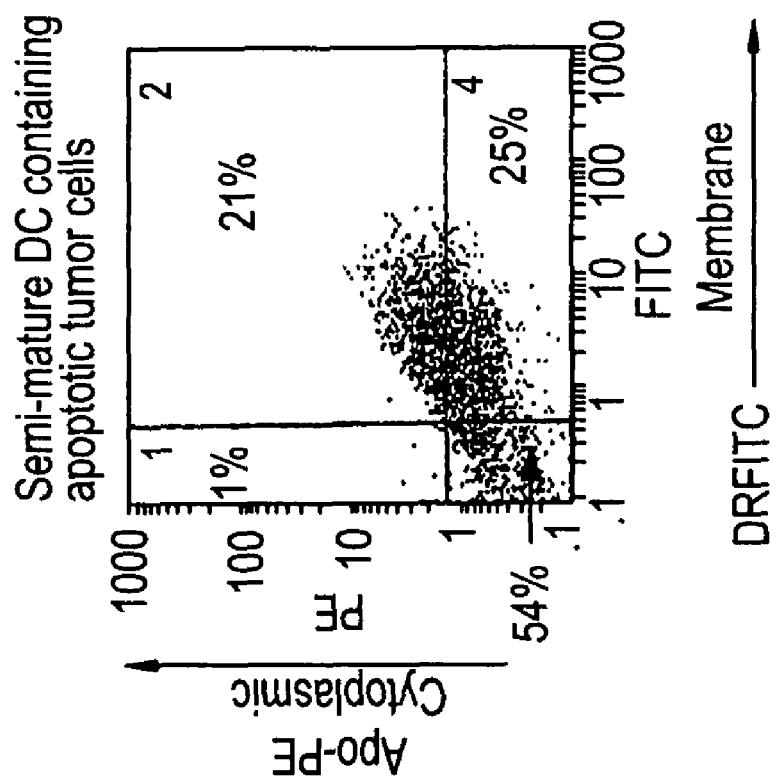
Figure 12C:
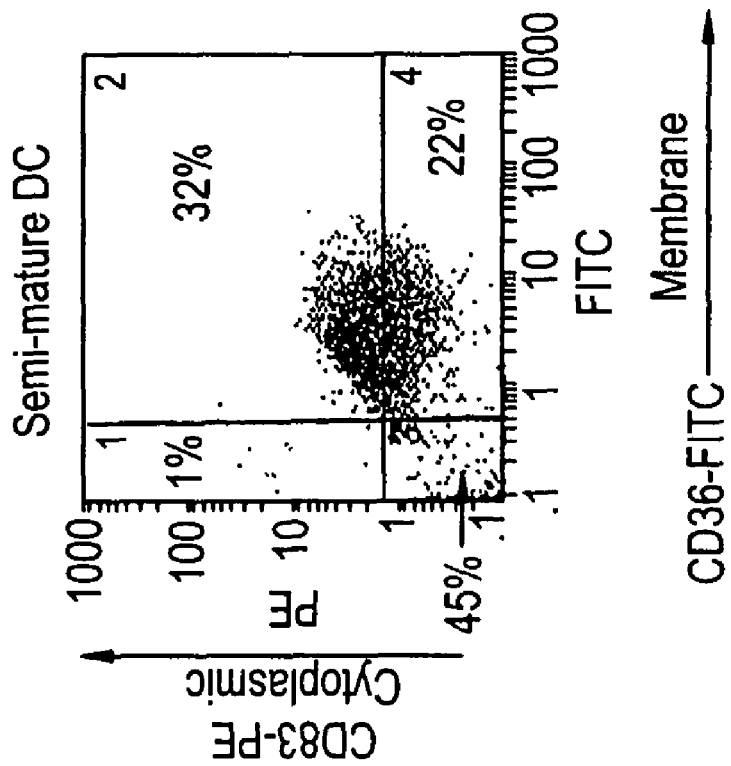
Figure 13A:
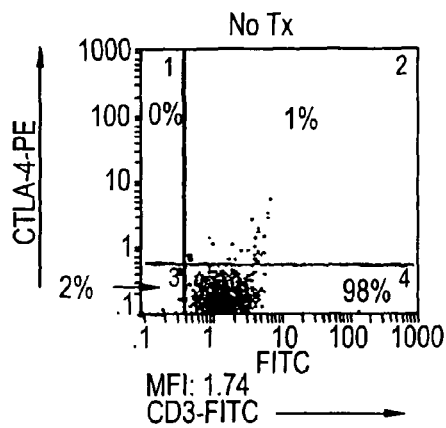
FIG. 13(a)-(f) are graphs showing the dependence of Treg preparation on exposure of normal CD4+ T cells to DCs fed apoptotic CTCL cells as measured by CTLA4, and CD25 expression.
Figure 13D:
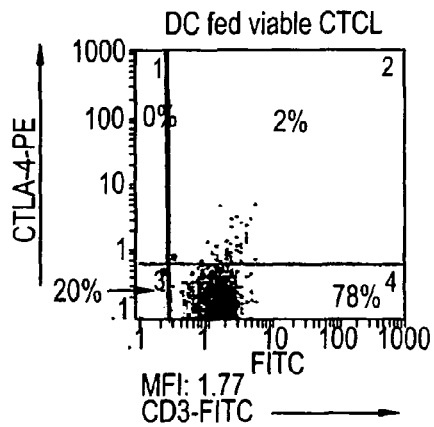
Figure 13B:
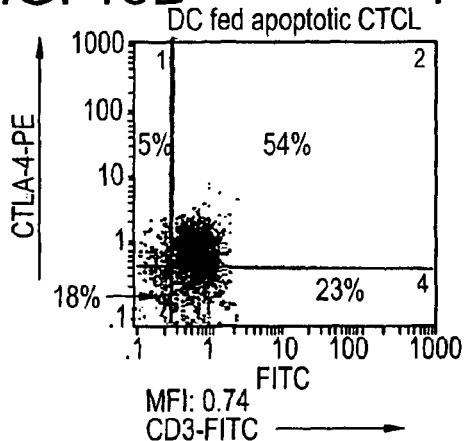
Figure 13E:
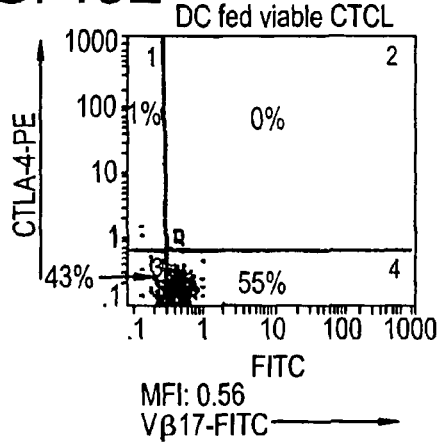
Figure 13C:
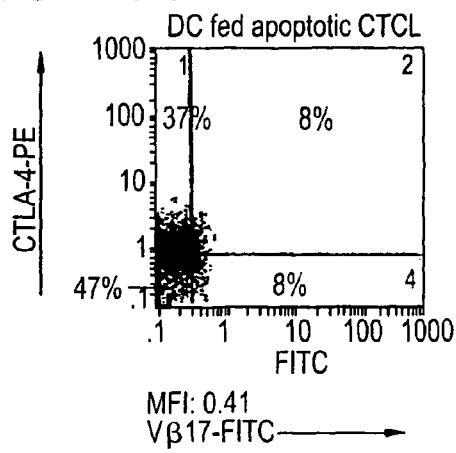
Figure 13F:
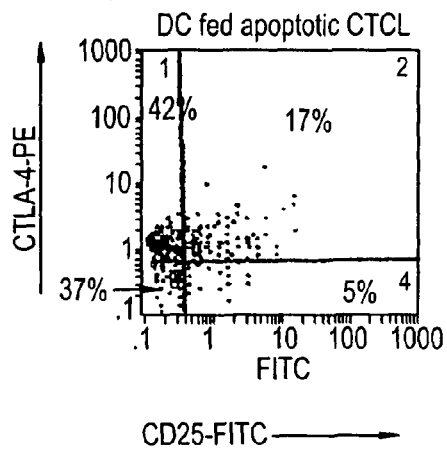

Turning now to FIG. 12 (*a*), in yet another aspect of this embodiment of the present invention, antigen presenting dendritic cells may be produced in a two-step process. Purified CD4+ CTCL cells 14 obtained using a packed column as described above are incubated with a CD3ab-conjugated material, typically a CD3ab-magnetic bead 52, which induces the CTCL cells to undergo apoptosis. The CD3ab-magnetic bead-apoptotic CTCL cell complex 52, 14 is collected in a filtration column 54 placed in a magnetic field 56, such is available from Miltenyi Biotech (Auburn, Calif.) as described above. Whole blood containing monocytes 12, or leukapheresed blood monocytes 12, are passed through the column 54 containing the apoptotic CTCL cells 50 complexed to the magnetic beads 50, 14. While not limiting the scope of the present invention, the inventors believe the monocytes begin to differentiate into DCs through the perturbations caused by the physical contact with the column, the beads, or both, as the monocytes flow through the column spaces, and through the phagocytosis of apoptotic CTCL cells. The CD3ab-magnetic bead-CTCL cell-monocyte complex is hereby included in the present invention as useful for inducing monocyte differentiation into DCs. Although not limiting the scope of the present invention, the inventors also believe that the differentiation of monocytes to DCs may be enhanced by the phagocytosis of the apoptotic CTCL cells (FIGS. 12(*b*) and (*c*)).

In still another aspect of this embodiment of the present invention, the differentiation of monocytes into DCs is achieved in a single-step process. This method comprises the step of providing a filtration column containing a CD3ab-conjugated material, typically a CD3ab-magnetic bead, and substantially contemporaneously passing whole blood or leukapheresed blood that contains both CTCL cells and monocytes through the column matrix. While not limiting the scope of the current invention, the inventors believe that the physical forces imposed on the monocytes as they flow through the packed column induce differentiation of the monocytes into DCs, and that the immature dendritic cells phagocytize apoptotic CTCL cells which are bound to the CD3ab-magnetic beads, which may further enhance monocyte differentiation to DCs.

As previously mentioned, it will be understood by one of ordinary skill in the art that the above described methods may be recombined or varied in sequence to achieve the desired result without departing from the scope of the current invention, and as such are hereby expressly included as embodiments of the current invention.

In another embodiment of the invention, functional DCs generated from blood monocytes through any of the methods of the present invention may be administered directly to a patient, typically the same donor patient, for the purpose of improving the patient's immunological state.

Figure 14A:
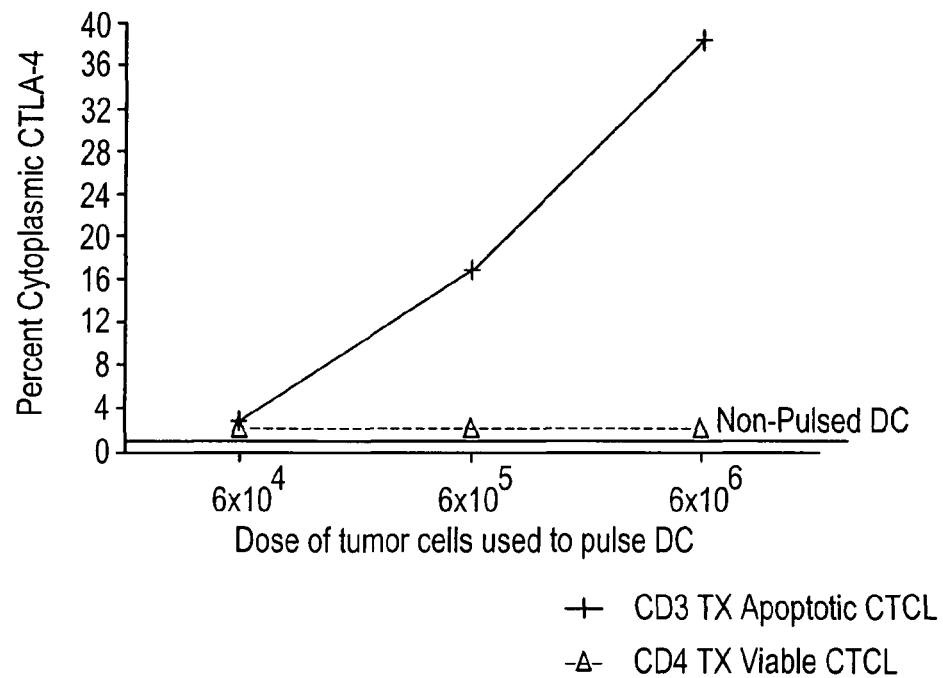
FIG. 14 is a graph showing the dependence of Treg preparation on (a) the dose of apoptotic tumor cells fed to DCs, and (b) the number of DCs exposed to the normal CD4+ CTCL cells; as determined by CTLA 4 expression.
Figure 14B:
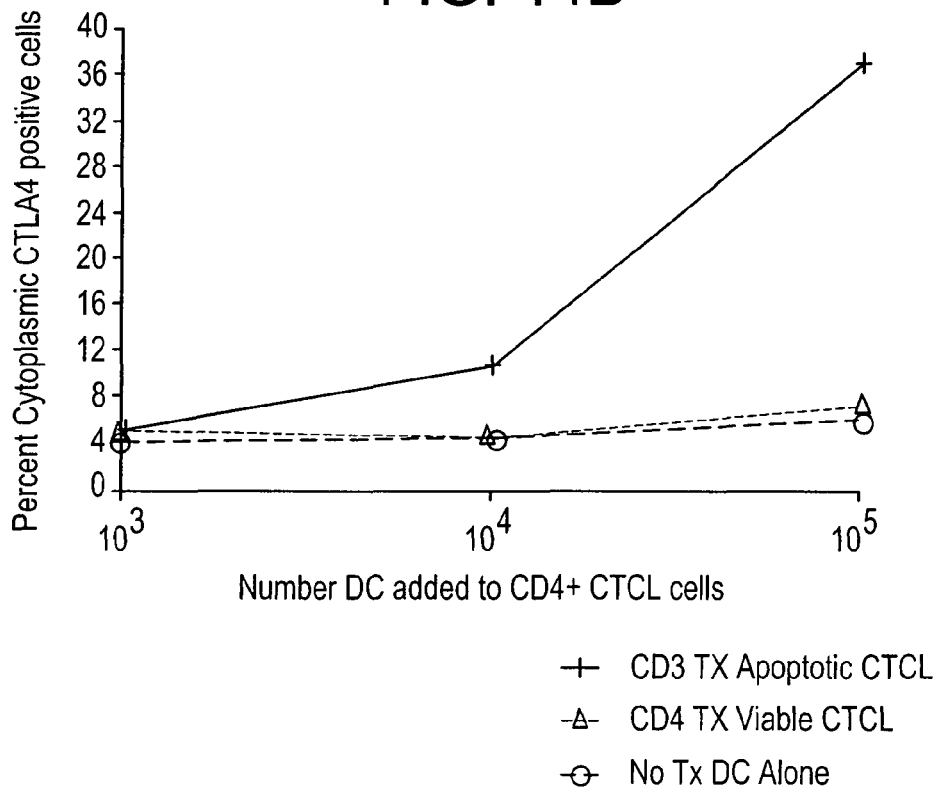
Figure 15A:
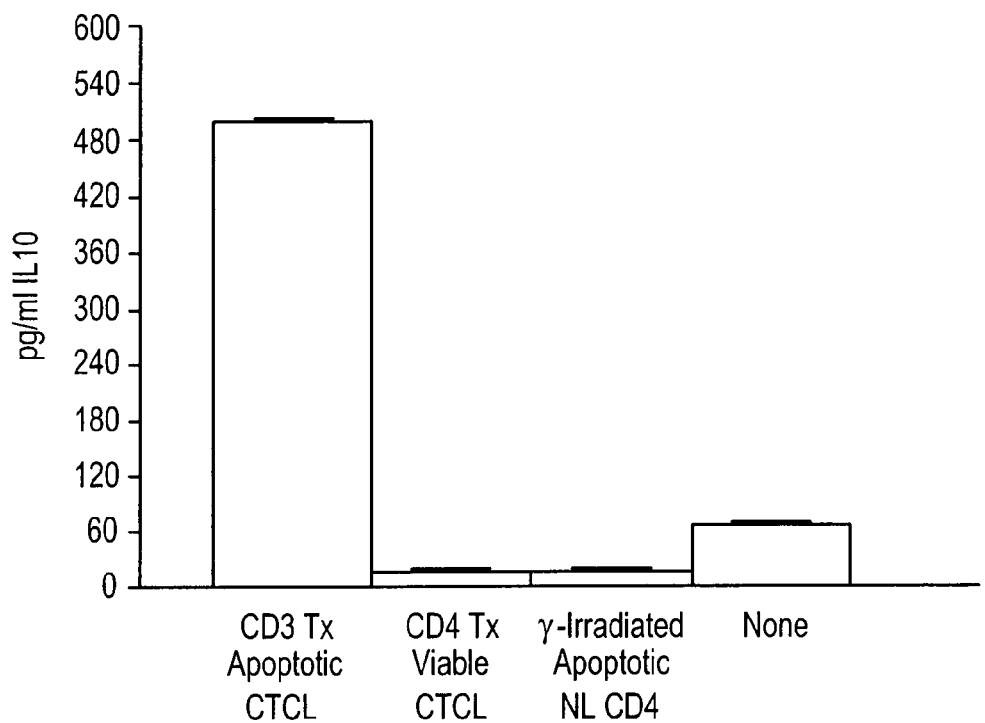
FIGS. 15(a) and (b) are bar charts showing measurements of (a) IL-10, and (b) TGF-0 production, indicating the Treg phenotype.
Figure 15B:
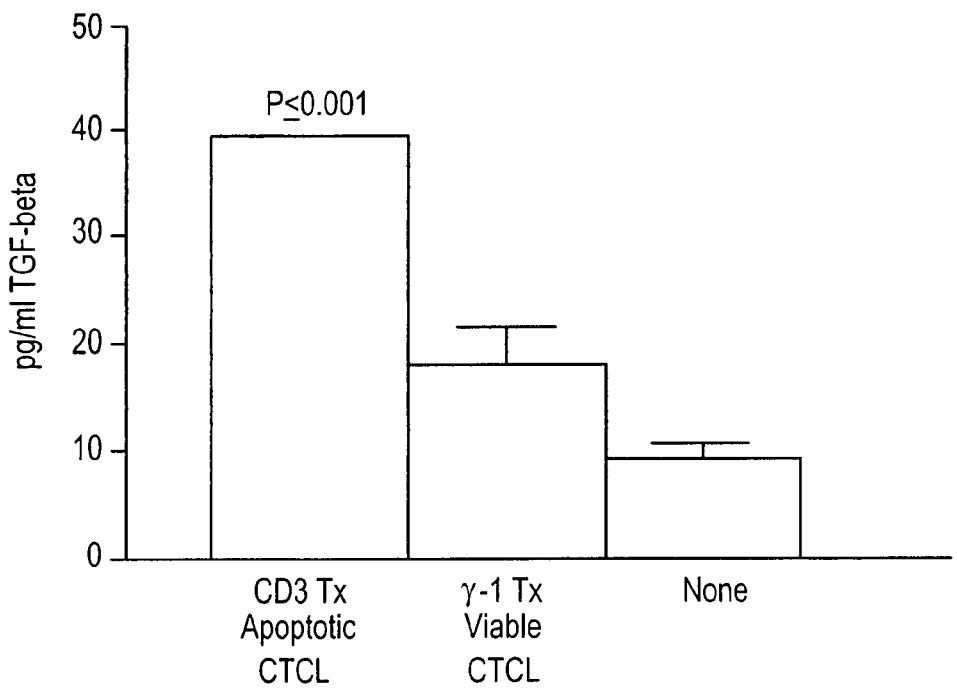

Turning now to FIGS. 13-15, in another embodiment of the methods of the present invention, DCs produced by induced differentiation of blood monocytes as described above and which have phagocytized apoptotic disease effector cells are exposed to normal CD4+ T cells to create T-cell regulatory cells (Tregs), which express cytotoxic T-cell lymphocyte antigen-4 (CTLA-4). FIG. 13 shows several graphs illustrating the production of Treg cells from exposure of normal CD4+ T cells to DCs fed apoptotic CTCL cells as measured by CTCL-4 expression. In one aspect of this embodiment, the blood monocytes are exposed to high levels of disease effector cells, for example, from about $5 \times 10^5$ to about $10 \times 10^6$ apoptotic effector cells, such as, for example, apoptotic CTCL cells, incubated with from about $1 \times 10^5$ to about $1 \times 10^6$ monocytes. In another aspect of this embodiment, leukapheresed blood is used to purify apoptotic disease effector cells for incubation with monocytes. In this manner the number of apoptotic disease effector cells could be increase by about an order of magnitude. In still another aspect of this embodiment, the monocytes are incubated with the apoptotic effector cells for about 12 hours to about 24 hours. In yet another aspect of this embodiment the resulting apoptotic CTCL-loaded DCs are incubated for about 12 hours to about 24 hours in the presence of CD4+ T cells, for example by incubation at 37 degrees Centigrade, to produce Tregs.

This embodiment of the invention is not limited to CTCL cells, and normal T cells exposed to DCs loaded with high numbers of apoptotic cells such as disease effector cells that cause autoimmune disease or transplant rejection can be induced to become T-regulatory cells. The Tregs formed by the exposure to apoptotic T cell-loaded DCs are hereby included as another embodiment of the current invention.

In another embodiment, the Tregs generated through any of the methods of the present invention may be administered to a patient, typically the same donor patient, for the purpose of improving the patient's immunological state. For example, the Tregs may be administered to a patient to treat autoimmune disorders such as pemphigus, lupus, diabetes or patients with graft rejection episodes. While not limiting to the scope of the current invention, the inventors believe that the Tregs may beneficially suppress a patient's immune system through physical interaction with T-cells via the CTLA-4 receptor ligand, as well as through paracrine mechanisms via secretion of IL-10, and TGF-β. FIG. 15 illustrates the levels of IL-10 and TGF-β production from cells produced by the methods described herein. This embodiment of the invention may be particularly suited to treatment of autoimmune diseases, and transplant tolerance by down regulating the patient's immune system.

As described above, in some embodiments of the invention, after monocyte differentiation has been induced, the treated blood may be incubated for a sufficient period of time to allow the DCs to develop to the desired stage of maturity prior to truncation of maturation. Incubation of the recipient DCs is performed using techniques known to those skilled in the art. The incubation may be performed in a suitable nutrient medium, and at a temperature from about 20 degrees Centigrade to about 50 degrees Centigrade. In a preferred embodiment, incubation is performed at approximately 37 degrees Centigrade in a standard incubator containing a gaseous environment having approximately 5% carbon dioxide and approximately 95% oxygen, with only trace amounts of other gases. Alternatively, incubation may be performed in a plastic blood bag as described above.

As will be appreciated by one of ordinary skill, the above-mentioned steps of: physical perturbation, incubation, and passage through a micro-column in the presence or absence of apoptotic cells may be combined and varied in sequence in any suitable manner, and are hereby expressly included as embodiments in the present invention.

In one aspect of the present invention, the relative maturity of a DC is assessed by determining the expression of certain marker polypeptides, for example MHC classII, CD83, CD36, DR or any combination thereof. Determination of the expression of marker polypeptides can be achieved through any suitable means known to those of ordinary skill, such as for example FITC-labeled antibodies, SDS-PAGE, ELISA or other suitable biochemical approach.

In each of the embodiments described above, the first step in the method may be preparation of a white blood cell concentrate from an extracorporeal quantity of the patient's blood in accordance with standard leukapheresis practice known to those skilled in the art. The white blood cell concentrate includes monocytes, lymphocytes and some red blood cells and platelets. Two billion white blood cells can typically be collected during leukapheresis. Assuming that monocytes comprise from about 2% to about 50% of the total white blood cell population collected, approximately 40 million to 1 billion monocytes are present in the white blood cell concentrate. The median monocyte percentage is approximately 20%, so commonly about 400 million monocytes will be in the white blood concentrate collected via leukapheresis.

While the invention is not limited to any particular mechanism of monocyte differentiation, it is believed that monocytes in the blood or blood cell concentrate are attracted to the polymeric surfaces of the column or column matrix, such as for example the plastic walls of the column or the polymeric "bead" matrix. While not limiting the scope of the current invention, the inventors believe that the column matrix may be more efficient for inducing monocyte differentiation than physical perturbation through rotation in a plastic tube alone, because the matrix material substantially increases the available surface area for contact by the monocytes. The tortuous fluid flow path through the column matrix imposes shearing forces on the transient and incompletely adhered monocytes, sending activation signals though the monocyte cell membrane, and inducing the differentiation of monocytes into functional DCs. Accordingly, as the monocytes pass through the column, they may undergo numerous episodes of transient adherence to, and release from the column matrix or column walls.

Induction of Monocyte Differentiation by Serum Proteins

In another embodiment of the invention, rather than removing serum proteins as described above, monocyte differentiation is induced utilizing the adherence of certain serum proteins, such as for example fibronectins or vitronectins, to induce differentiation of the monocytes. Monocyte differentiation into dendritic cells can also be initiated by signals received through the cell membrane. Fibronectins and vitronectins are proteins contained in plasma of the bloodstream. These serum proteins can provide signals to monocytes, after binding monocyte membrane receptors, helping to stimulate monocyte differentiation into dendritic cells. In vivo, one of the functions of proteins such as fibronectin and vitronectin is to adhere to the cells lining the inner surface of blood vessels. As blood containing monocytes flows past the protein bearing vessel wall, monocytes contained in the blood come into contact with and adhere to the protein, an initial step contributing to the capacity of these white blood cells to leave the blood vessels and migrate into the surrounding tissue. The monocytes accomplish this migration by pulling themselves, by a process known as "diapedesis," between the endothelial cells which line the capillaries and other blood vessels. The transmigratory process, abetted by the binding of fibronectins, vitronectins and related proteins, to monocyte membrane receptors, contributes to the maturation of monocytes into dendritic antigen presenting cells, capable of stimulating often specific immune reactions.

It has been discovered that serum proteins such as fibronectin and vitronectin contained in blood plasma will also adhere to the surface of plastics, such as those used in a photopheresis device or in a device constructed to treat blood in the transimmunization process, such as a photopheresis device, a plastic treatment apparatus or a packed column as described above. In the case of a packed column, the column should be packed with a plastic packing media, such as for example plastic beads. The fibronectin and vitronectin adhered on the surface of the plastic transmits signals to monocytes flowing past the proteins causing the monocytes to differentiate into dendritic cells. The differentiation of monocytes is enhanced in the transimmunization process because of the large plastic surface accessible to a large number of monocytes procured through this extracorporeal procedure. The interaction of the passaged monocytes to the proteins adherent to the plastic surface is reminiscent of the in vivo interaction of monocytes with proteins adherent to endothelial cells of blood vessels. Similarly, the stimulation of monocyte maturation into dendritic cells through such interaction with serum proteins such as fibronectin or vitronectin coating the photopheresis device plastic surface is reminiscent of the in vivo maturation of monocytes into dendritic cells, as contributed to by this process in intact mammals. As a result, a large number of processed blood monocytes can be stimulated to become dendritic cells, entering this maturational pathway within one day after being so processed. These newly formed dendritic cells have various therapeutic uses, enhanced by the synchronicity of their level of maturation. It should be noted that this process work in conjunction with, and be complementary to, physical perturbation of the monocytes in the treatment device to induce differentiation of blood monocytes into dendritic cells.

Because serum proteins such as fibronectin and vitronectin are abundantly found in plasma, the plastic surfaces of the device used for the transimmunization procedure are readily exposed to the proteins during the photopheresis process. To coat the plastic surface with proteins such as fibronectin and vitronectin, it is important that the blood containing plasma be pumped through the treatment device. Monocytes can be simultaneously pumped through the treatment device together with the plasma containing the serum proteins. Alternatively, the monocytes can be separated from the plasma, and the plasma may be pumped through the treatment device to condition the plastic surface with proteins such as fibronectin and vitronectin. The proteins adhere to the surface of the plastic, and the monocytes are then pumped through the treatment device and pass close to the protein conditioned plastic. The monocytes receive a signal from the proteins to contribute to their differentiation into functional dendritic cells.

In a preferred embodiment, an extracorporeal quantity of blood is obtained from a subject. The extracorporeal quantity of blood is treated by leukapheresis as described above to obtain a leukocyte concentrate comprising monocytes and plasma containing proteins including fibronectin and vitronectin. The monocytes and protein containing plasma are pumped together through a treatment device of the types described above (i.e. photophersis device, plastic treatment apparatus or packed column). The treatment conditions, such as flow rates, temperatures and treatment times, are preferably as described above for each type of device. It is understood, however, that one skilled in the art may alter these parameters as appropriate to achieve a desired result.

At least some of the proteins contained in the plasma adheres to the plastic surfaces and interacts with passing monocytes. The proteins, in particular the fibronectin and vitronectin, signal the monocytes to differentiate and form dendritic cells. Following treatment in the treatment device, the monocytes are incubated for variable times, up to three days. As described above, the monocytes may be coincubated with disease effector cells that have been rendered apoptotic or inactive to allow the dendritic cells to phagocytize the disease effector cells. The disease effector agents may also be presented to the dendritic cells using biodegradable particles as described in U.S. patent application Ser. No. 10/884,519, the contents of which are hereby incorporated in their entirety. The incubated monocytes may be administered to the subject or frozen for later use.

In another embodiment of the invention, a treatment device is first conditioned using blood plasma obtained from a subject to coat the surface of the device with serum proteins including fibronectin and vitronectin. In this embodiment, the extracorporeal quantity of blood is first treated using a leukapheresis device to obtain a leukocyte concentrate. The leukocyte concentrate is then further treated to separate the blood cells, including the monocytes, from the plasma. This treatment step can be performed using any technique known to those skilled in the art, such as for example using centrifugal elutriation, a density gradient or by immunoselection.

The plasma component containing proteins including fibronectin and/or vitronectin is pumped through the treatment device to condition the plastic surfaces of the device with the proteins. The quantity of plasma pumped through the device is selected to achieve a desired level of fibronectin and/or vitronectin adhered to the plastic surface. The can be determined based upon the concentration of the proteins in the plasma and the surface area of the plastic surface. Preferably, the plasma is pumped through the treatment device under conditions (temperature, flow rates, volumes, etc.) such as those described above. It is understood, however, that one skilled in the art may alter these parameters as required to achieve a desired result. At least some of the fibronectin and vitronectin in the plasma adheres to the plastic surface. Monocytes obtained from the extracorporeal quantity of blood are then pumped through the treatment device where they are exposed to the proteins adhered to the surface of the plastic. The fibronectin and vitronectin signals the monocytes to differentiate and form dendritic cells. After passing through the treatment device, the monocytes are incubated to allow differentiation of the monocytes to proceed. If desired, the monocytes may be co-incubated with disease effector cells that have been rendered apoptotic or inactive as described above. The incubated monocytes may be administered to the subject or frozen for later use.

As will be recognized by those skilled in the pertinent art based upon the teachings herein, numerous changes and modifications may be made to the above-described and other embodiments of the invention without departing from its scope as defined in the appended claims. Accordingly, this detailed description of preferred embodiments is to be taken in an illustrative as opposed to a limiting sense.

What is claimed is:

1. A method for inducing the differentiation of monocytes in an extracorporeal quantity of a subject's blood into dendritic cells comprising the steps of:
    (a) obtaining an extracorporeal quantity of a subject's blood;
    (b) treating the extracorporeal quantity of blood by leukapheresis to obtain a white blood cell concentrate comprising monocytes and plasma containing proteins;
    (c) pumping the white blood cell concentrate through a treatment device having plastic channels; and
    (d) after step (c), incubating the white blood cell concentrate for a sufficient time to allow differentiation of the monocytes to a dendritic cell phenotype.

2. The method of claim 1, wherein the plasma containing proteins comprises at least one of fibronectin or vitronectin.

3. The method of claim 2, wherein the white blood cell concentrate is pumped through the treatment device for a period of between about 15 minutes to about 3 hours at a temperature of between 35 degrees Centigrade to 40 degrees Centigrade.

4. The method of claim 3, further comprising the step of selecting or isolating dendritic cells from the treated white blood cell concentrate based upon the presence of a substantially dendritic-cell specific polynucleotide, polypeptide or both.

5. The method of claim 2, further comprising the step of combining the white blood cell concentrate with apoptotic disease effector cells after step (c) and prior to step (d).

6. The method of claim 5, wherein the white blood cell concentrate and the apoptotic disease effector agent are incubated together for a period of between 6 hours and 72 hours at a temperature of between 35 degrees Centigrade and 40 degrees Centigrade.

* * * * *